(12) United States Patent
Danielsson et al.

(10) Patent No.: US 7,440,539 B2
(45) Date of Patent: Oct. 21, 2008

(54) X-RAY PROTECTION DEVICE

(75) Inventors: Mats Danielsson, Täby (SE); Torbjörn Hjärn, Vaxholm (SE)

(73) Assignee: Sectra Mamea AB, Kista (SE)

( * ) Notice: Subject to any disclaimer, the term of this patent is extended or adjusted under 35 U.S.C. 154(b) by 0 days.

(21) Appl. No.: 10/928,098

(22) Filed: Aug. 30, 2004

(65) Prior Publication Data

US 2005/0078797 A1    Apr. 14, 2005

(30) Foreign Application Priority Data

Mar. 1, 2002    (SE) ................................ 0200654

(51) Int. Cl.
*H01J 35/16*    (2006.01)

(52) U.S. Cl. .................... 378/37; 378/147; 378/150; 378/151; 378/203

(58) Field of Classification Search ............ 378/37, 378/203, 145, 147, 150, 151; 250/505.1, 250/507.1, 515.1, 519.1
See application file for complete search history.

(56) References Cited

U.S. PATENT DOCUMENTS

| | | | |
|---|---|---|---|
| 3,659,108 A * | 4/1972 | Quase ................... 250/506.1 |
| 4,090,084 A | 5/1978 | Epstein et al. |
| 4,122,350 A | 10/1978 | Lipthay et al. |
| 4,157,476 A * | 6/1979 | O'Connor .................... 378/203 |
| 4,203,037 A * | 5/1980 | Gur et al. ...................... 378/37 |
| 4,343,997 A * | 8/1982 | Heinz ...................... 250/505.1 |
| 4,825,455 A | 4/1989 | Bauer |
| 4,852,141 A * | 7/1989 | Horn .......................... 378/147 |
| 4,943,991 A | 7/1990 | Mosby |
| 4,998,270 A * | 3/1991 | Scheid et al. ................ 378/155 |
| 5,037,374 A * | 8/1991 | Carol ............................ 600/1 |
| 5,040,202 A * | 8/1991 | Scheid ........................ 378/155 |
| 5,594,769 A * | 1/1997 | Pellegrino et al. ............. 378/37 |
| 6,175,117 B1 * | 1/2001 | Komardin et al. ...... 250/363.06 |
| 6,325,538 B1 | 12/2001 | Heesch |
| 6,470,072 B1 * | 10/2002 | Johnson ...................... 378/154 |
| 6,768,783 B2 * | 7/2004 | Eriksson et al. ............... 378/37 |

* cited by examiner

*Primary Examiner*—Allen C. Ho
(74) *Attorney, Agent, or Firm*—Novak Druce + Quigg LLP

(57) ABSTRACT

A shielding arrangement for an x-ray apparatus, preferably for mammography examination is disclosed, and comprises at least an x-ray source, a collimator arrangement and a detector assembly, whereby the collimator is arranged between the x-ray source and the detector assembly and through which x-rays pass. The shielding arrangement, at least partly made of x-ray blocking material and provided for blocking, scattering and/or reflecting x-rays is arranged, at least partly, in a space between the x-ray source and collimator.

9 Claims, 5 Drawing Sheets

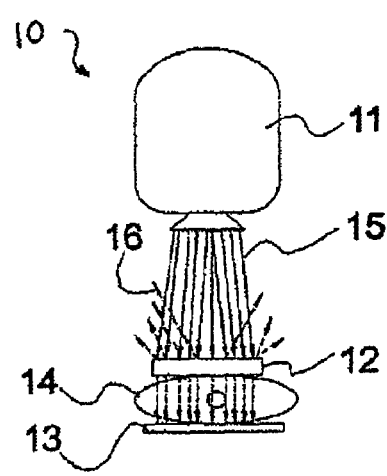
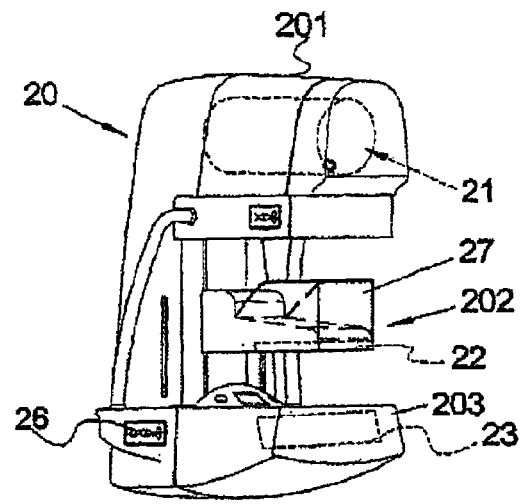
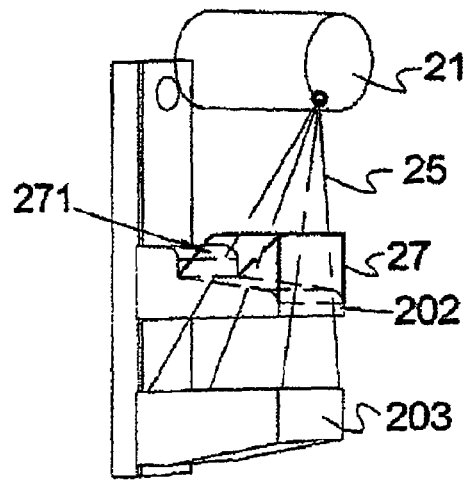
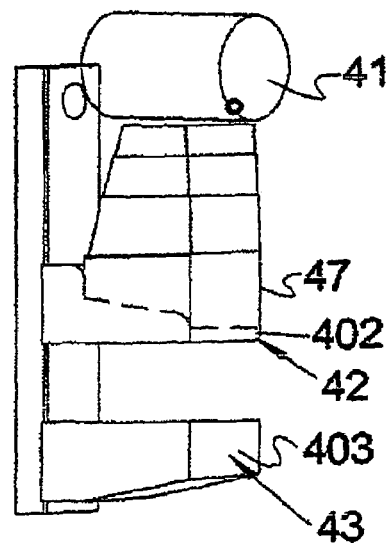
FIG. 1
FIG. 2
FIG. 3
FIG. 4

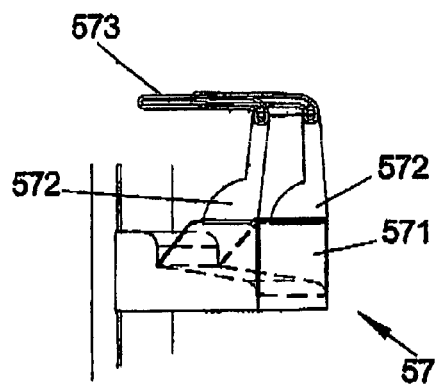
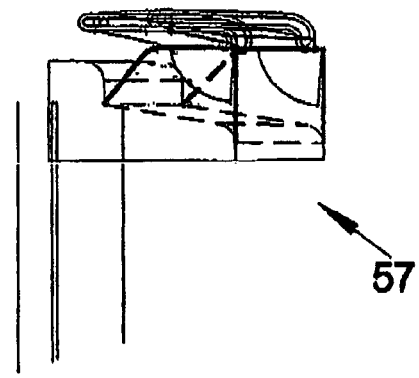
FIG.5     FIG.6
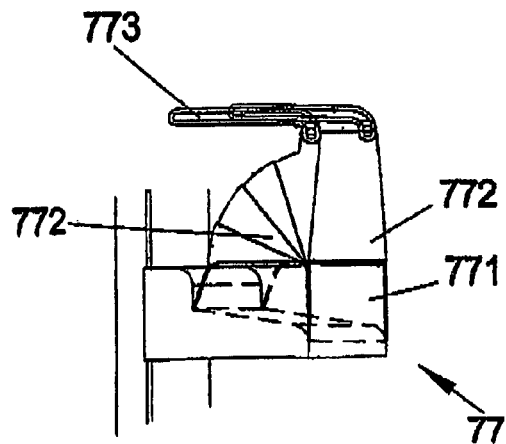
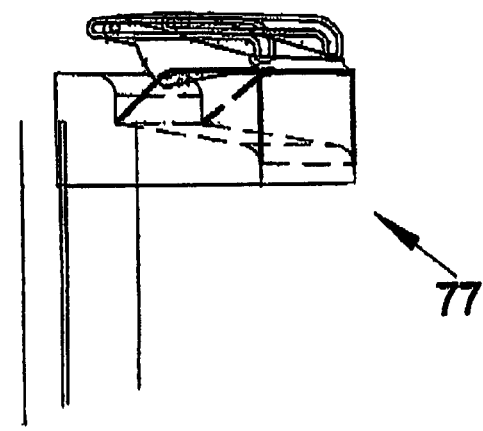
FIG.7     FIG.8

X-RAY PROTECTION DEVICE

TECHNICAL FIELD OF THE INVENTION

The present invention relates to a shielding arrangement in an x-ray imaging apparatus for mammography, for protecting a patient (person to be examined) and the operator (nurse) against scattered and reflected x-rays.

More specially, the invention relates to x-ray apparatuses, which at least comprise an x-ray source, a collimator arrangement and a detector assembly, whereby said collimator is arranged between said x-ray source and said detector assembly and through which x-rays pass.

BACKGROUND OF THE INVENTION

When examining persons by means of x-ray, especially for mammography, the person and the operator are usually exposed to scattered and reflected x-rays.

FIG. 1 is a schematic side view of a digital mammography apparatus 10 comprising a radiation source 11, a collimator 12 and a detector assembly 13. The breast 14, to be examined is pressed to and flattened between the paddles containing the collimator and detector assembly. The x-rays 15 from the source 11 are collimated by the collimator 12 and pass through the breast 14 and heat the detector assembly. However, some of the x-ray incident to the collimator is reflected and scattered. The scattered/reflected beams are denoted with number 16. These beams are scattered in all direction, here also into the plane of the drawing and out of the plane of the drawing (not shown). There are also some rays that scatter from the source 11.

The undesired radiation can be up to 1 m/Gray, and usually occur between the x-ray source and the collimator. Thus, the there may occur two different radiation strengths: one before the collimator and one after the collimator. The radiation is stronger before the collimator, and the person to be examined must be protected.

Prior art disclose different arrangements for protecting a person at mammography examination. For example U.S. Pat. No. 4,090,084 relates to a mammography apparatus and more particularly to the means for compressing a pressure plate of the apparatus against the breast. The mounting of the pressure plate is such that the pressure can be applied uniformly throughout the breast area. To enable such uniform pressure to be obtained, the pressure plate is connected at its opposite ends to slide means which slide on tracks mounted on the cone of the X-ray machine. For the determination of the thickness of the compressed breast tissue between the pressure plate and the film upon which the breast rests, a measuring rod is secured to the tracks and a pointer is attached to the means which move on the tracks.

In this case, the collimator is an oblong, conical unit, which extends from the x-ray source to pressure plates. Thus, the collimator is not displaceable. The pressure plate is displaceable and the shield is arranged as a part of the pressure plate.

Another arrangement is disclosed in U.S. Pat. No. 4,122,350, according to which an adjustable collimator is provided for use in mammography in which there is a mounting ring for securing the collimator to an x-ray source; a collimating cone having a plurality of leaves, each pivotably secured at one end thereof to said mounting ring and positioned in overlapping relationship to one another to define at their opposite ends a substantially kidney shaped opening through which x-rays may be directed to a female breast positioned below said cone; and a collar positioned about and capturing the plurality of leaves and to be raised and lowered along the leaves relative to said mounting ring to adjust the size of the opening.

This document describes an adjustable collimator extending from the x-ray source to a supporting plate. The collimator, by means of a displaceable collar, can be adjusted to direct the x-rays to a female breast. No particular radiation shields are used. However, a non-conductive sheet (S) draped from the collimator and is placed between the collimator and the breast to protect the breast from contacting the collimator.

SUMMARY OF THE INVENTION

Thus, the main object of the present invention according to preferred embodiments is to reduce or eliminate the amount of the scattered/reflected in x-ray apparatus, especially for mammography apparatus having a collimator unit, mainly a vertically adjustable collimator unit, arranged between the breast and the x-ray source. Another object according to a preferred embodiment is to prevent reduction of the area that the x-rays hit the examined object because of the shielding arrangement. Moreover, the shielding must be so arranged that it does not become inconvenience for the patient by taking unnecessary space. The shielding must also be arranged so that it can be positioned before exposure to x-ray but after that the collimator/paddle has been adjusted and positioned over for example a female breast. From a functional point of view, this requires an automatic shielding arrangement that can assume at least two positions: one for exposure period (above the collimator/paddle) and one for collimator/paddle adjustment (out of way).

Therefore, the initially mentioned x-ray apparatus between said x-ray source and collimator comprises a shielding arrangement for blocking scattering and/or reflecting x-rays. In a preferred embodiment, the shielding arrangement is a box-shaped structure provided on a housing for said collimator. According to another embodiment, the shielding arrangement is a telescopic structure between said x-ray source and collimator. In yet another embodiment, the shielding arrangement is a concertina folding structure between said x-ray source and collimator. The shielding arrangement is at least partly made of an x-ray blocking material. Preferably, the collimator provided with said shielding arrangement and said detector arrangement are displaceable relative each other, the collimator provided with said shielding arrangement and said x-ray source are displaceable relative each other.

In one preferred embodiment, the shielding arrangement comprises a number of boxes insertable into each other, with varying sizes. The largest box is closest to the collimator, and at least one wall of each box is inclined. This allows shielding along the entire way from the x-ray source to the pressure plate, no blocking of x-rays and also a comfortable design for the patient. Of course, it is possible to have the opposite size configuration.

Thus, the invention relates to a shielding arrangement in an x-ray apparatus, at least comprising an x-ray source, a collimator arrangement and a detector assembly, whereby said collimator is arranged between said x-ray source and said detector assembly. The shielding arrangement, at least partly made of x-ray blocking material and provided for blocking scattering and/or reflecting x-rays is arranged, at least partly, in a space between in said x-ray source and collimator.

The invention also relates to a method in an x-ray apparatus, preferably for mammography examination, at least comprising an x-ray source, a collimator arrangement and a detector assembly, whereby said collimator is arranged between said x-ray source and said detector assembly, for blocking scattering and/or reflecting x-rays, comprising arranging a shielding arrangement for blocking said scattering and/or reflecting x-rays between said x-ray source and collimator.

BRIEF DESCRIPTION OF THE DRAWINGS

In the following, the invention will be further described in a non-limiting way with reference to the accompanying drawings in which:

FIG. 1 schematically illustrates a mammography x-ray apparatus,

FIG. 2 is a perspective view of a preferred embodiment of the invention,

FIG. 3 is a schematic perspective view of the embodiment in FIG. 2, illustrating shielding and x-ray path, FIG. 4 is a perspective view of a second embodiment of the invention, FIGS. 5 and 6 are perspective views of a third embodiment of the invention, FIGS. 7 and 8 are perspective views of a third embodiment of the invention.

DETAILED DESCRIPTION OF THE EMBODIMENTS

Figure 10:
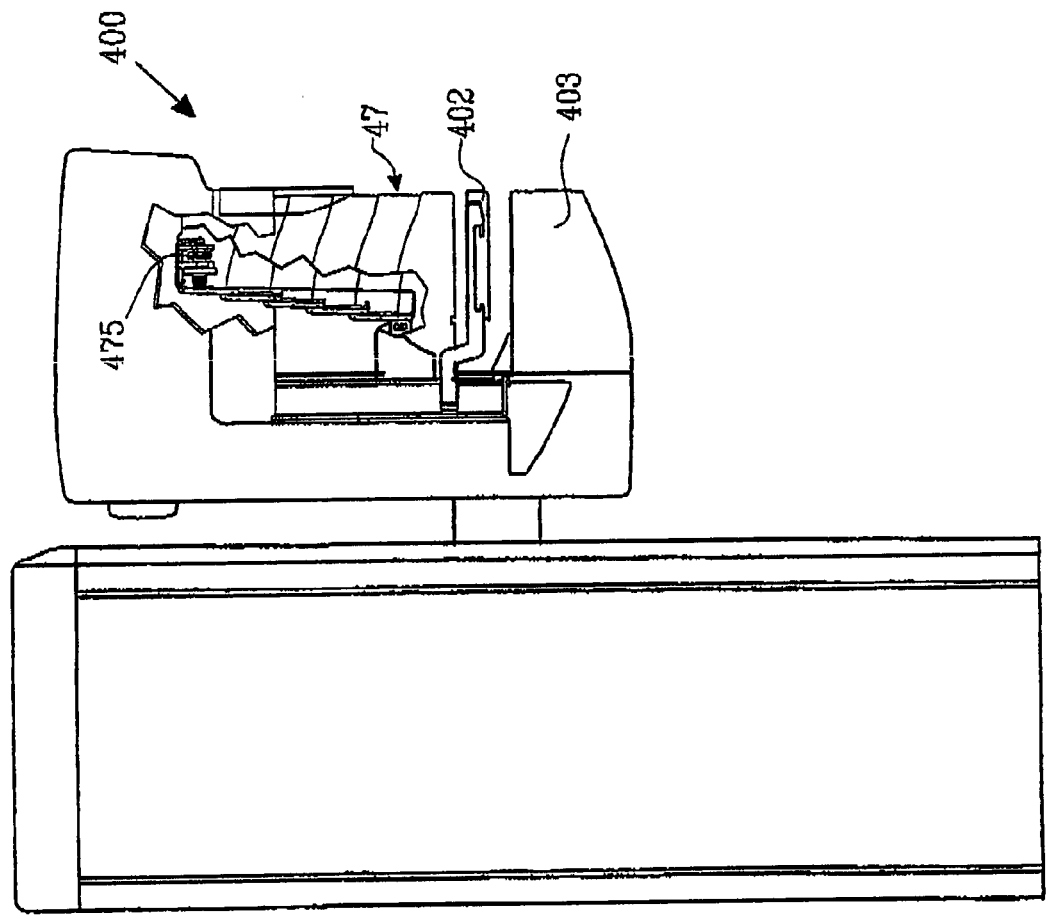
FIG. 10 is a side view of the shielding arrangement according to FIGS. 4 and 9, FIGS. 11 and 12 are schematic views of a the shielding arrangement in different positions.

One preferred embodiment of the invention is illustrated in FIG. 2. Part of a digital x-ray apparatus 20, which normally is provided on a support (not shown) comprises a housing 201, inside which an x-ray source 21 is provided. The housing also comprises additional parts (not shown) for controlling the x-ray generation, control of the apparatus etc. The apparatus comprises a paddle or pressure plate arrangement 202 and a support 203 both extending laterally from a vertically oriented support member (not labeled), as shown in FIG. 2. A collimator assembly 22 is provided inside the paddle 202 and a detector assembly 23 inside the support 203. Hence, the collimator and detector are both laterally extending from and supported by the vertically oriented support member. Preferably, the detectors comprise of electrode strips arranged on a substrate and tilted with respect to the incident x-rays, or gaseous detectors.

The paddle 202 (and hence the collimator assembly 22) and the support 203 are displaceable relative each other, and relative the x-ray source; especially, the paddle 203 can be lowered and elevated in a vertical direction. A breast (or other body parts, not shown) of a person to be examined can be placed between the paddle and the support. A number of control switches 26 for controlling the paddle movement and other apparatus functions are arranged on the housing.

To reduce or eliminate the scattered/reflected x-rays, a shielding arrangement 27 in form of a frame or box is arranged on the upper side of the paddle/collimator 202/22, i.e. the side that the paddle is exposed to the x-rays from the x-ray source 21. The frame substantially covers the entire edge of the upper paddle surface. The frame is made of an x-ray blocking material, such as lead, wolfram, etc. or a material containing an x-ray blocking material, in such a substantial amount that it blocks x-rays to pass the frame structure. The frame has a dimension that provides shielding both in the lowest position, i.e. closest to the support and the highest position, i.e. closes to the x-ray source. FIG. 3 shows a schematic view illustrating the x-ray path 25 through the frame 27. Like reference characters refer to same parts as in FIG. 2. According to this embodiment, the frame has three perpendicular sides one inclining side 271. Thus it allows exposure of substantially the entire support surface 203 to x-rays. However, the frame can be constructed with respect to the focusing of the x-ray from the source 21.

One advantage of the location of the frame is that the entire part 20 shown in FIG. 2 can be arranged movable, e.g. sidewise through pivoting around an axis (not shown) and still offering protection.

A second embodiment is schematically illustrated in FIG. 4. This embodiment will be described more closely in relation to FIG. 9 forward. The shielding arrangement 47 is a telescopic frame extending between the x-ray source 41 and the collimator/paddle 42. A detector assembly 43 (not shown) is arranged inside the support 403. Through its telescopic structure, it allows shielding between the entire distance from the x-ray source to the paddle. It is also possible to arrange a curtain shaped shielding, e.g. in shape of accordion folding, made of a flexible material containing x-ray blocking material.

A third embodiment of the invention is illustrated in FIGS. 5 and 6. The shielding arrangement 57 comprises a base portion 571, two substantially L-shaped side portions 572 each connected to an upper part such as the x-ray source housing (not shown) through links 573. The links 573 are provided with grooves in which pegs arranged at the ends of the L-shaped side portions. The side portions are arranged pivoting to the base portion. FIG. 6 shows the shielding arrangement 57 folded when it is in its upper position close to the x-ray source. The lower end of the L-shaped portion, which is substantially circle sector shaped, pivots inside the base portion. This arrangement allows more protection as it blocks more of the scattering beams.

A fourth embodiment of the invention is illustrated in FIGS. 7 and 8. The shielding arrangement 77 is similar to the one according to FIG. 5 and comprises a base portion 771, two sectors of a circle and fan shaped side portions 772 each connected at upper part to the x-ray source housing (not shown) through links 773. The links 773 are provided with grooves in which pegs arranged at the ends of the fan shaped side portions can be moved. The side portions are arranged foldable. FIG. 8 shows side portions of the shielding arrangement 77 folded when it is in its upper position close to the x-ray source.

Figure 9:
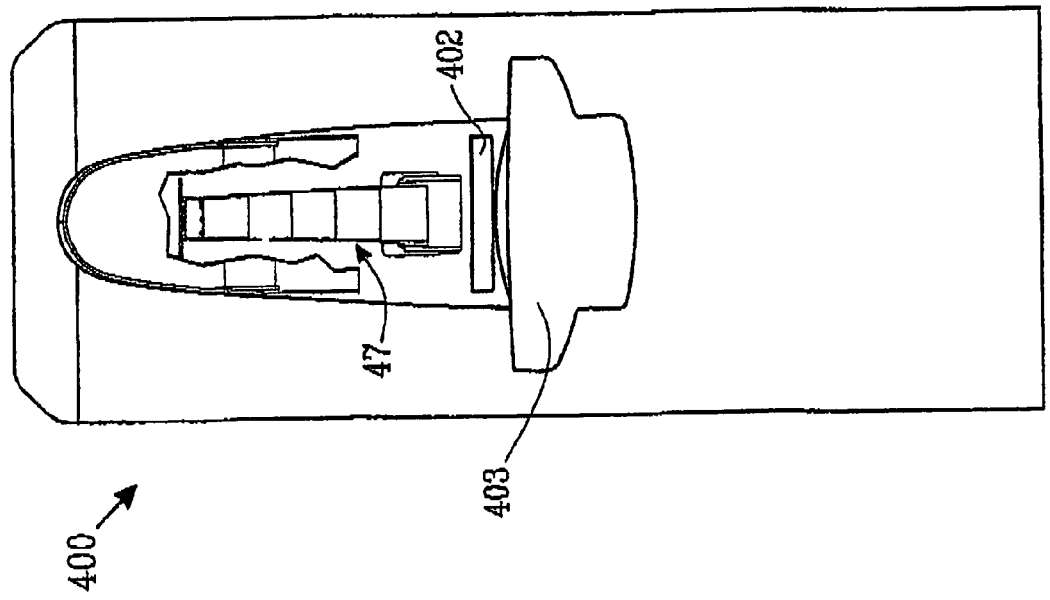
FIG. 9 is a frontal view of the shielding arrangement according to FIG. 4.

The arrangement of FIG. 4 is illustrated in more detail in FIGS. 9 and 10, showing frontal and side views, respectively of the x-ray apparatus 400. Parts of the housing and shield are cut away to illustrate the shield 47 structure. The telescopic shield comprises a number of boxes 471 having different sizes: the one closes to the paddle 403 being the larges and the one closest to the source being the smallest. A driving mechanism 475 is arranged to fold and unfold the boxes when the paddle is displaced vertically.

Figure 12:
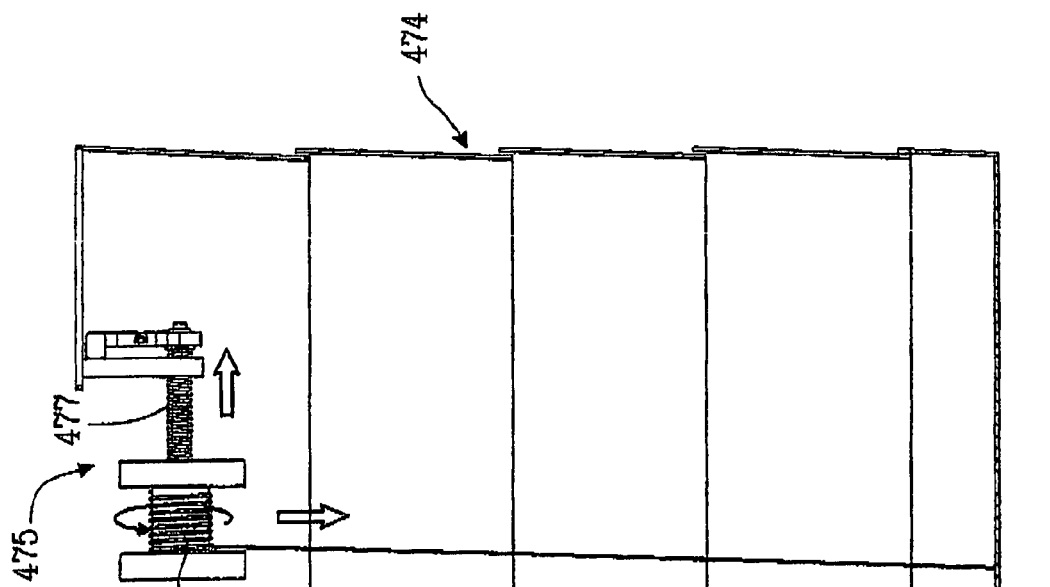
Figure 11:
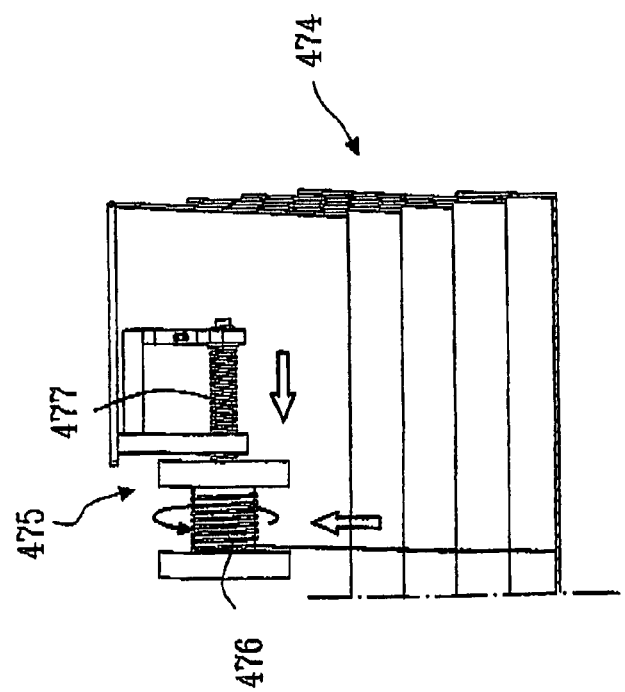

As mentioned above, the shielding arrangement should not disturb the x-ray path from the source to the collimators. Thus, the shield must have substantially same boundary in all positions of the paddle. Inclining at least one side of the boxes, as illustrated in the schematic FIGS. 11 and 12 solves the problem. FIG. 11 shows the shielding retracted and FIG. 12 extracted. In this case, the wall 474 of the box facing the patient is inclined and thus allows the walls to slide into each other along a straight line without interrupting the x-ray path. Of course, the distance between the walls in a real arrangement is much smaller prohibiting the x-rays to leak through walls. The space between the walls can be provided with sealing in forma of bends, flexible curtains, agents, etc. the driving mechanism in this case is very schematically illustrated comprising a winding 475 and a liner driver shaft 477. This may also allow pulling the boxes inwardly (FIG. 11), i.e. a traverse movement. It is a possible to traverse the boxes more that the frontal walls' inclination. Thus, the joints of the telescopic structure becomes very tight at the extracted position and blocks x-ray leak, and at the same time that a good mechanical play is obtained for retraction.

Obviously, alternative driving mechanisms and locations for the same can occur.

Figure 13:
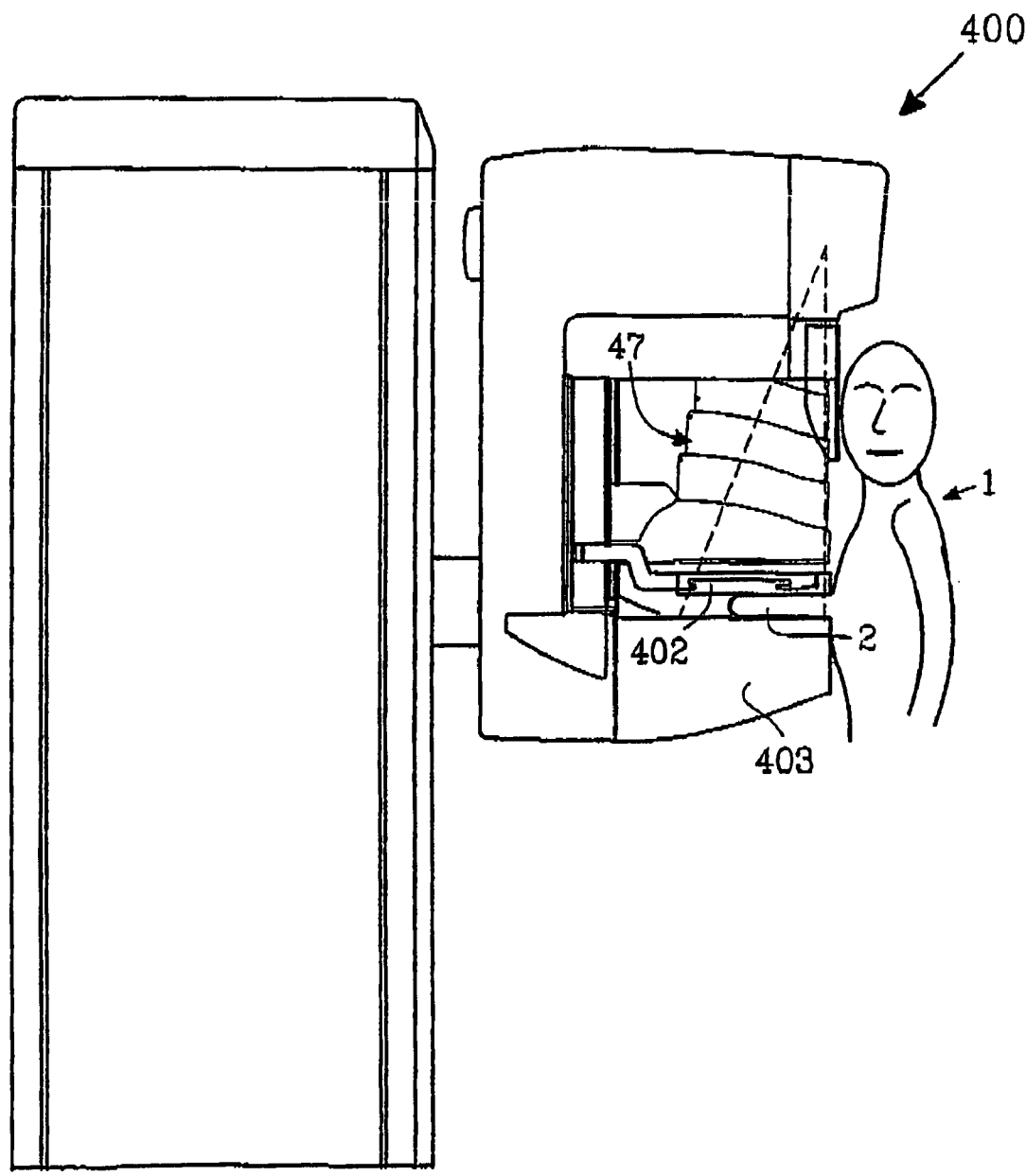
FIG. 13 is an operational view of a mammography apparatus comprising a shielding arrangement according to one aspect of the invention.

FIG. 13 illustrates schematically the x-ray apparatus 400 having a shielding arrangement according to FIG. 4 in operation when examining a female 1 breast 2.

The invention is not limited to the shown embodiments but can be varied in a number of ways without departing from the scope of the appended claims and the arrangement and the method can be implemented in various ways depending on application, functional units, needs and requirements etc.

The invention claimed is:

1. An x-ray apparatus, comprising:
   a vertically oriented support member;
   a collimator and a detector assembly supported by and extending laterally relative to said vertically oriented support member with said collimator disposed above and vertically displaceable relative to said detector assembly;
   an x-ray source disposed above said collimator and said detector assembly with said collimator being arranged between said x-ray source and said detector assembly in such a way that x-rays pass through said collimator; and
   a shielding assembly arranged between said x-ray source and said collimator, wherein said shielding assembly and said x-ray source are displaceable relative to each other.

2. The x-ray apparatus according to claim 1, wherein said shielding assembly is a box-shaped structure provided on a housing for said collimator.

3. The x-ray apparatus according to claim 1, wherein said shielding assembly is a telescopic structure between said x-ray source and said collimator.

4. The x-ray apparatus according to claim 1, wherein said shielding assembly is an accordion shaped folding structure between said x-ray source and collimator.

5. The x-ray apparatus according to claim 1, wherein said shielding assembly is at least partly made of an x-ray blocking material.

6. The x-ray apparatus according to claim 1, wherein said collimator provided with said shielding assembly and said detector arrangement are displaceable relative to each other.

7. The x-ray apparatus according to claim 1, wherein said shielding assembly is displaceable substantially vertically.

8. An x-ray apparatus, comprising:
   a vertically oriented support member;
   a collimator and a detector assembly supported by and extending laterally relative to said vertically oriented support member with said collimator disposed above said detector assembly;
   an x-ray source disposed above said collimator and said detector assembly with said collimator being arranged between said x-ray source and said detector assembly in such a way that x-rays pass through said collimator; and
   a shielding assembly arranged between said x-ray source and said collimator, wherein said shielding assembly and said x-ray source are displaceable relative to each other;
   wherein said shielding assembly comprises a number of boxes insertable into each other, with varying sizes, the largest box being closest to the collimator.

9. The x-ray apparatus according to claim 8, wherein at least one wall of each box is inclined.

* * * * *